(12) United States Patent
Nelson

(10) Patent No.: US 8,152,731 B2
(45) Date of Patent: Apr. 10, 2012

(54) WAVELET TRANSFORM AND PATTERN RECOGNITION METHOD FOR HEART SOUND ANALYSIS

(75) Inventor: Alex T. Nelson, Portland, OR (US)

(73) Assignee: Inovise Medical, Inc., Beaverton, OR (US)

( * ) Notice: Subject to any disclaimer, the term of this patent is extended or adjusted under 35 U.S.C. 154(b) by 867 days.

(21) Appl. No.: 11/704,403

(22) Filed: Feb. 8, 2007

(65) Prior Publication Data

US 2007/0191725 A1 Aug. 16, 2007

Related U.S. Application Data

(60) Provisional application No. 60/772,046, filed on Feb. 10, 2006.

(51) Int. Cl.
*A61B 5/02* (2006.01)

(52) U.S. Cl. ...................................................... 600/528

(58) Field of Classification Search .................. 600/507, 600/509, 513–517, 523
See application file for complete search history.

(56) References Cited

U.S. PATENT DOCUMENTS

| | | | |
|---|---|---|---|
| 5,218,969 A * | 6/1993 | Bredesen et al. ............. | 600/523 |
| 7,039,538 B2 | 5/2006 | Baker, Jr. | |
| 7,171,269 B1 | 1/2007 | Addison et al. | |
| 2004/0127792 A1 | 7/2004 | Siejko et al. | |
| 2004/0230105 A1 * | 11/2004 | Geva et al. ..................... | 600/301 |
| 2005/0222515 A1 * | 10/2005 | Polyshchuk et al. .......... | 600/528 |
| 2007/0055151 A1 * | 3/2007 | Shertukde et al. ............ | 600/437 |
| 2007/0167846 A1 * | 7/2007 | Sternickel et al. ............ | 600/509 |

OTHER PUBLICATIONS

USPTO Office Action for U.S. Appl. No. 12/321,646 dated Jun. 17, 2011. 9pp.
USPTO Office Action for U.S. Appl. No. 12/288,712 dated Apr. 11, 2011. 5pp.
USPTO Office Action for U.S. Appl. No. 12/321,647 dated Jun. 1, 2011. 7pp.
USPTO Office Action for U.S. Appl. No. 12/321,650 dated Sep. 7, 2011. 8 pp.
USPTO Office Action for U.S. Appl. No. 12/005,555 dated Dec. 23, 2010. 7pp.

* cited by examiner

*Primary Examiner* — Niketa Patel
*Assistant Examiner* — Michael D Abreu
(74) *Attorney, Agent, or Firm* — Jon M. Dickinson, Esq.; Robert D. Varitz, Esq.

(57) ABSTRACT

A wavelet transform and pattern recognition method for analyzing a subject's heart sounds including (a) obtaining subject-related heart-sound data utilizing a first sampling rate, (b) obtaining simultaneously existing subject ECG data, including pre-selected ECG fiducial data, and (c) processing such obtained data including, relative to the heart-sound data, (1) computing the maximum-overlap discrete wavelet transform (MODWT) for a preselected number of wavelet scales, (2) locating the peaks in time of the absolute values of the MODWT coefficients respecting each of a such scales, and (3), for each such scale, (i) interpolating between the located peaks, and (ii) subsampling each interpolation result at a second sampling rate which no greater than the mentioned first sampling rate.

12 Claims, 1 Drawing Sheet

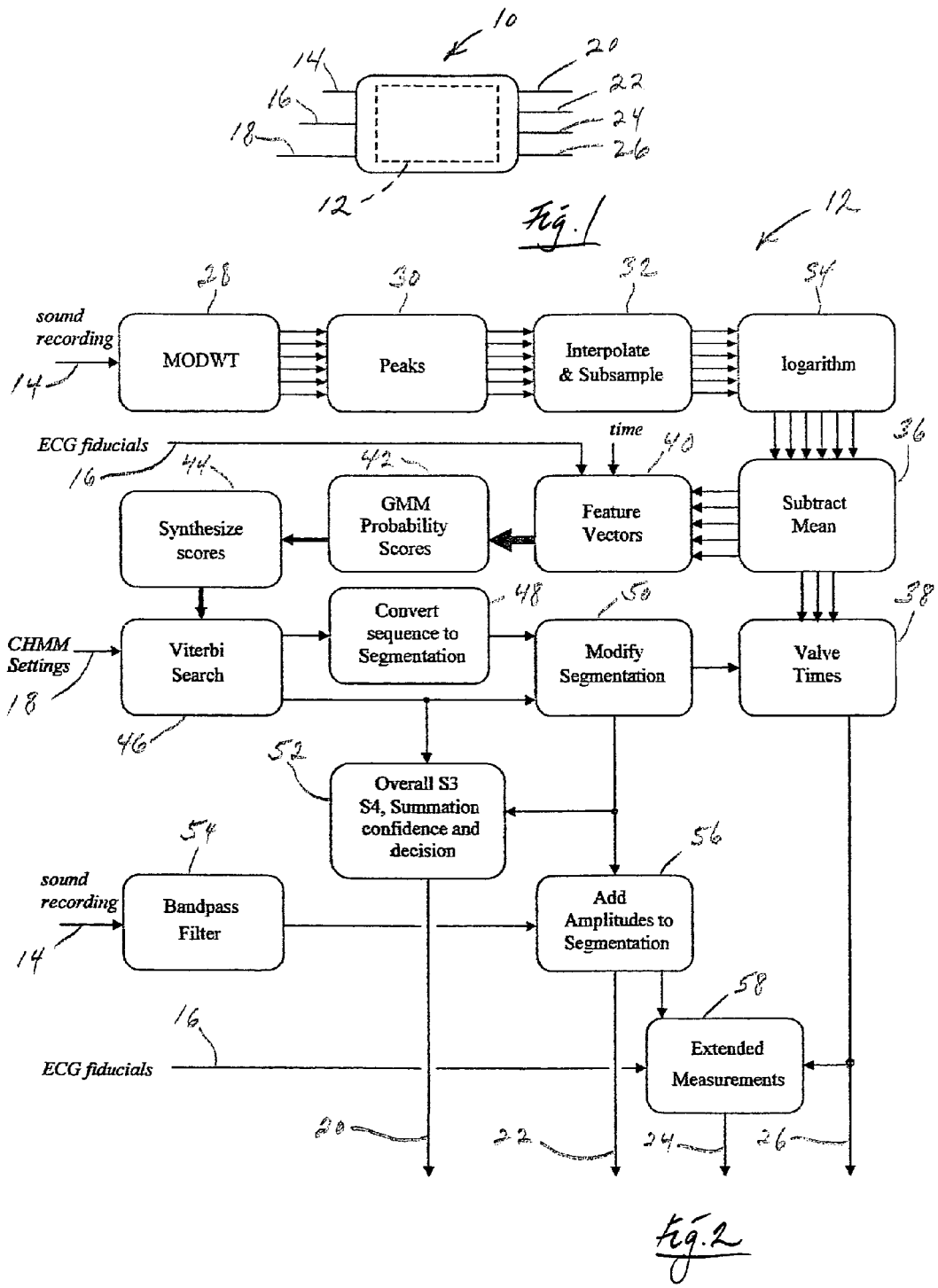

WAVELET TRANSFORM AND PATTERN RECOGNITION METHOD FOR HEART SOUND ANALYSIS

CROSS REFERENCE TO RELATED APPLICATION

This application claims priority to prior-filed, currently U.S. Provisional Patent Application Ser. No. 60/772,046, filed Feb. 10, 2006, for "Wavelet Transform and Pattern Recognition Method for Heart Sound Analysis". The entire disclosure content of that Provisional Application is hereby incorporated herein by reference.

DEFINITIONS

CHMM settings. In the practice of the present invention, there are four such settings. These include: (a) penalty to prevent two S1 sounds from occurring within the same heartbeat (as defined by the interval between successive QRS onsets); (b) penalty to prevent S3 sounds from starting too soon or too late after the start of an S2 sound; (c) modifications to transition probabilities that prevent the S1, S2, S3 and S4 heart-sound times from starting at inappropriate times relative to QRS onset times; and (d) interbeat dependence which is a function that boosts the probability score of a sound at a beat-relative time if the same sound scored highly on previous beats at the same beat-relative time. The natures of these settings are familiar to those skilled in the art.

Extended measurements. In the practice of the present invention, there are four employed extended measurements. These include: (a) the well-known quantity EMAT, which is the time duration from a QRS onset to the associated, so-called S1 valve time; (b) % EMAT which is the ratio of EMAT divided by the duration from an R-peak time to the next successive R-peak time; (c) LVST which is the time duration measured between the so-called S1 and S2 valve times; and (d) % LVST—a term which relates to the ratio of LVST divided by the duration from an R-peak time to the next successive R-peak time.

Feature vector. This term, as employed herein, is something which is calculated via a series of processing operations which will be more fully explained in the detailed description of the invention below.

Heart sounds. Also referred to herein as sound components, heart sounds include the usual, recognized S1, S2, S3, S4 heart-produced sounds.

Wavelet scale. A wavelet scale, as that term is employed herein, is effectively a band of frequencies computed by a Length-8 wavelet filter drawn from the Daubechies Least Asymmetric family of wavelet filters, with this band being bounded on its opposite ends by the minus 3-db points in the associated frequency band relative to the operation of the relevant filter. Six wavelet scales, I-VI, inclusive, are involved Scale I extends from about 124-Hz to about 250-Hz. Scale II extends from about 62-Hz to about 124-Hz. Scale III covers a frequency band extending from about 31-Hz to about 62-Hz. Scale IV extends from about 16-Hz to about 31-Hz. Scale V extends from approximately 8-Hz to approximately 16-Hz. Finally, scale VI includes a band of frequencies extending from about 4-Hz to about 8-Hz.

Temporal window frame. With respect to each wavelet scale, a temporal window frame has a length herein of about 50-milliseconds. A series of temporal window frames, generally speaking, is a series associated with a particular wavelet scale. Overlapping. With respect to each wavelet scale, there is an associated plurality of temporal window frames each having the length just mentioned above, and each overlapping one another in time whereby the beginning of each frame occurs about 12-milliseconds after the beginning of the previous frame (assuming, of course, that there is a previous frame).

In the structure and the operation of the present invention, a certain kind of subsampling operation takes place with regard to these respective wavelet scales, with the sampling rate for scale I being about 500-Hz, that for scale II being about 250-Hz, that for scale III being about 166.67-Hz, that for scale IV being about 83.33-Hz, that for scale V being about 41.67-Hz, and that for scale VI being about 21.74-Hz.

BACKGROUND AND SUMMARY OF THE INVENTION

In the field of cardiology, there is strong and significant interest in utilizing the ever-improving capabilities of computer-based digital signal processing to aid in assessing the condition of the human heart and the associated cardiovascular system. The present invention is aimed at that interest.

In this context, the invention offers a unique, and informationally powerful, methodology featuring a wavelet-transform and signal-pattern recognition approach which draws relevant cardio-condition information from heart-sound data that is correlated in various ways with synchronized, ECG, electrical-signal fiducials. Preferably, though not necessarily, the source heart-sound and ECG data are derived non-invasively from a human subject.

As one will learn on reading the below descriptive disclosure of this invention, the invention is characterized by a number of innovative facets. With respect to these facets, the invention is easily visualized and made understandable, and thus made readily practice-accessible to the so-motivated users, by the block-schematic illustrations provided in the two drawing-figure illustrations of the invention. Individual building blocks used in these figures to present the important architecture of the invention methodology may, per se, be entirely conventional in internal construction and operation, but their cooperative, interrelated overall assembly and interactive operation(s) is/are unique. The above-mentioned invention facets are defined by different sub-portions of this overall assembly.

Accordingly, the various advanced features and advantages of the invention will now become more fully apparent as the description of the invention which follows is read in conjunction with the associated drawings.

DESCRIPTION OF THE DRAWINGS

FIG. 1 is a simplified and very high-level block/schematic diagram of the overall architecture of the preferred embodiment of, and manner of practicing, the present invention.

FIG. 2 provides a more detailed block/schematic presentation of the invention architecture which is illustrated in FIG. 1. Each individual block in FIG. 2 is, per se, conventional and familiar to those who are generally skilled in the relevant art. For this reason, the respective, internal make-ups of these blocks are not further detailed herein.

DETAILED DESCRIPTION OF THE INVENTION

Turning now to the drawings, and beginning with FIG. 1, indicated generally at 10 is a single block which represents the overall architecture of a preferred embodiment of, and manner of practicing, the present invention. Block 10, as a whole, takes the form of an appropriate, programmed, software-algorithm-controlled digital computer, within which, as illustrated by a dashed-lined rectangle 12, resides the operative, architectural algorithm of the invention. This algorithm carries out the central, wavelet-transform and signal pattern-recognition functionalities of the invention. Three inputs to block 10 and to algorithm 12 are shown generally at 14, 16, 18, and four, relevant, processed information outputs from block 10 and algorithm 12, are shown generally at 20, 22, 24, 26.

Input 14 furnishes, preferably, non-invasive, heart-sound signals and data, in any suitable, conventional manner, from a human subject. Input 16 furnishes, preferably, non-invasively collected electrical ECG fiducial information which information is also delivered, simultaneously, in any suitable conventional manner, from the same human subject. Input 18 furnishes conventional CHMM (Constrained Hidden Markov Model) settings associated with the same human subject. These CHMM settings have been defined earlier and above herein.

Adding attention now to FIG. 2 in the drawings, this figure elaborates both the core structure and the operating methodology of the invention, as such are embodied and realized in algorithm 12. As can be seen in this figure, heart-sound input 14, and ECG fiducial-data input 16, each feeds input information to two different recipient locations in algorithm 12. Algorithm 12, per se, includes sixteen word-labeled, operatively interconnected structural and functional blocks 28-58 (even numbers only), inclusive. Each of these blocks herein in FIG. 2 is internally conventional in construction, and the operations and structures of these blocks, which may take on a number of different conventional forms, are well understood by those generally skilled in the relevant art.

The locations of previously described inputs and outputs are clearly marked in FIG. 2, and with respect to inputs 14 and 16, and as was just earlier suggested herein, each of these two inputs connects, effectively, to two locations within the block diagram of FIG. 2 which represents algorithm 12. Very specifically, heart-sound information provided by input 14 is supplied to blocks 28, 54 in FIG. 2, and ECG fiducial information, or data, is supplied by input 16 to blocks 40, 58. Made clearly evident in FIG. 2 are the operative, information-flow interconnections, or paths, which exist between the several blocks, with these signal-flow paths being illustrated by single-headed arrows which describe the directionality of signal flow, and therefore of signal processing flow.

With respect to interconnections that exist between blocks 28 and 30, 30 and 32, 34 and 36, and 36 and each of blocks 38, 40. These interconnections are represented by collections of plural signal-flow arrows, with all of these arrow-"collections"-connections being six in number between (a) block 28, 30, (b) blocks 30 and 32, (c) blocks 32, 34, and (d) blocks 34, 36. This number of connections—six is related to the above-mentioned six wavelet scales which are employed in the practice of this invention. Between blocks 36, 38, the collection of signal-flow arrows is only three in number, and between blocks 36, 40, five in number. The reasons for the less-than-six numbers of connections existing between blocks 36, 38 and blocks 36, 40 will be explained shortly.

As can be seen particularly well in FIG. 2, with respect to the four, previously-mentioned outputs, output 20 comes from block 52, and provides output information related to the text which appears within the image of block 52 in FIG. 2. Output 22, similarly, provides information characterized by the language which appears in the image of block 56 in FIG. 2 to which it is connected. Outputs 24 26, respectively, provide output information as identified by the texts appearing, respectively, in the images of blocks 58, 38, respectively, to which these two outputs are connected.

With heart-sound and ECG fiducial data, and appropriate CHMM settings information, introduced as identified in FIG. 2 into algorithm 12 via inputs 14, 16, 18, the wavelet transform and pattern recognition methodology of this invention for analyzing a subject's heart sounds takes place, as is now described.

When an analysis is to be made in accordance with the practice of this invention respecting the condition of a subject's heart, an appropriate time frame, such as a time frame of about 10 seconds, is selected for the gathering of heart-sound and ECG fiducial data, preferably performed non-invasively. Heart-sound data is and acquired by the conventional technique of digital sampling, and this is done at a rate preferably of about 500-Hz—a rate which has been found to be quite suitable. This 500-Hz sampling rate is also referred to herein as a first defined sampling rate. Sampled heart sound information is fed via input 14 to blocks 28 and 54 in FIG. 2. Simultaneously, ECG fiducial information is also appropriately gathered, prepared and delivered, as seen in FIG. 2, to blocks 40 and 58. CHMM settings data, described earlier herein, is furnished via input 18 to block 46 in FIG. 2.

With respect to the operation of block 28 on received heart-sound information, this block computes what is referred to herein as the maximum-overlap discrete wavelet transform (MODWT), also known in the art as a stationary wavelet transform, specifically to develop wavelet scales I-VI, using, as mentioned above in the definitions sections of this disclosure, the conventionally known Length-8 wavelet filter from the Daubechies Least Asymmetric Family of wavelet filters. These six, developed wavelet scales are then fed from block 28, via the six arrow-headed connections shown extending between blocks 28, 30, to block 30 which functions to locate, in time, the peaks of the absolute values of the MODWT coefficients for each wavelet scale.

Following the operation of block 30, wavelet scale information relevant to what has taken place within this block is furnished, as illustrated in FIG. 2, first to block 32, and thence through block 32 to block 34. Within block 32, and for each wavelet scale, an interpolation takes place between the peak information developed within block 30. Subsampling for each wavelet scale is then performed with respect to interpolated signal information at a uniform sampling rate which, under all circumstances, is no greater than the mentioned first defined sampling rate of 500-Hz. In fact, subsampling performed here which is relevant to the six different wavelet scales is performed at specifically different sampling rates, the values of which are related to the specific frequency bands associated with each of the six different wavelet scales. Reference here is made back to the Definitions section of this disclosure for a reminder at this point of how the wavelet scales are frequency-banded, and what specific subsampling rates, also referred to herein as second defined sampling rates, are specifically employed with respect to each of the six different wavelet scales.

Within block 34, a mathematical operation is performed to compute the logarithms of the uniformly sampled values developed by the operation of block 32. Logarithmic information developed by the operation of block 34, for each of the six wavelet scales, is furnished to block 36 which then computes the average of all log values within each wavelet scale, with this average then being subtracted from each log value on a wavelet-scale-by-wavelet-scale basis.

Looking at the flow of information which emerges from block 36, and which is supplied to block 40, here one will note, as mentioned earlier, that only five arrowheaded lines are employed to illustrate this communication path. The reason for this is that, at this point in the operation of this invention, the only information transmitted between blocks 36, 40 is that information which relates to wavelet scales II-VI, inclusive.

Several important operations take place within the confines of block 40. More specifically, within this block a computation takes place to develop a series of what are referred to herein as feature vectors, and this is done by aggregating the log values developed in the operation of block 36 within a series of 50-millisecond temporal windows, referred to herein as window frames, or just as frames. Specifically, the chosen frames for this purpose overlap with one another in such a fashion that the beginning of each frame is timed to take place about 12-milliseconds after the beginning of a previous frame, assuming, of course, that there has been a previous frame. This results in a feature vector which is computed in this fashion being generated essentially every 12-milliseconds.

Also taking place within the operation of block 40 is the act of appending to each vector the following three elements: (a) the time from the previous QRS onset to the time at the middle of the relevant frame; (b) the time from the previous P-wave onset to the beginning of the frame; and (c) the time from the end of the relevant time frame to the time of the beginning of the subsequent QRS onset.

Still describing what occurs within block 40, for each frame, the first three elements of each vector are replaced by a linear transformation of those three elements. This transformation consists of multiplying the three-element sub-vector by an appropriate matrix designed, approximately to diagonalize the co-variance matrix of the first three elements of each vector, as computed across all frames of all data. In the relevant and well understood art, which is, per se, conventional art, this practice is known as a whitening transformation.

Finally, with respect to the operation of block 40, for each frame, there is appended to the vector as delta features the temporal difference between consecutive wavelet values, but only with respect to wavelet scales III, IV and V.

Within block 42, which receives output information from block 40, and for each frame, a computation takes place to determine the multidimensional probability density function for each sound candidate (S1, S2, S3, S4). These functions are embodied by a Gaussian mixture model, and the output of each density function is referred to herein as a score.

From block 42, processed signal information is fed to block 44, wherein, by using the median of the seven highest scores in each frame, a synthesis of the scores takes place for sound candidates which do not have explicit probability density function models. This synthesizing process, and the nature of the resulting output information following synthesis, is well understood by those skilled in the art.

Output information from block 44 flows as shown to Viterbi search block 46 which also receives the previously mentioned CHMM settings data via input 18. Using the CHMM information, and a Viterbi search, processing takes place to compute the posterior probability of each sound candidate occurring during each frame, given all of the available data, and for the purpose of finding the maximum likelihood sequence of candidate sounds evident in the available data.

From block 46, output information is fed, as can be seen in FIG. 2, to blocks 48, 50 and 52.

Within block 48 a conversion takes place to convert the sequence of heart sounds into a desired segmentation of the input and received heart-sound data.

Within block 50 a modification of the segmentation performed in block 48 takes place to ensure consistency of sounds between different cardiac cycles. Here, any heart-sound S3 and S4 segments which are found to have abnormal timing, or which are followed by apparent excessive noise, are omitted from further treatment.

Outputs from block 50 are supplied, as shown, to blocks 38, 52 and 56.

Within block 38, and only in relation to wavelet scales numbers I, II and III, the first and second valve closure times within each previously identified heart-sound S1 and heart sound S2 segment are determined using information supplied from block 36. In block 56 a determination is made respecting the amplitude of the bandpass-filtered waveform within each segment. The relative bandpass filter as employed herein has a highpass cutoff at about 22-Hz and a lowpass cutoff at about 125-Hz. The amplitude is the difference between the highest and lowest values in the relevant segment.

In block 52, a determination is made to establish the overall presence or absence of heart sounds S3 and S4, and of summation sounds based upon all the available data. Also determined within this block is the overall confidence of scores associated with those S3 and S4 determinations. This overall confidence score for each sound is formed by summing the probability scores from individually identified S3, S4 and summation segments, respectively, along with the scores of heartbeats which did not contain such segments. This determined, overall confidence score is then compared to a suitable, user-selectable threshold so as to determine the overall presence or absence of the relevant heart sound.

Finally, within block 58, and based upon the several inputs provided this block as seen in FIG. 2, calculations take place to establish what were previously described as extended measurements. Such calculations are quite familiar to those skilled in the relevant art.

Thus, from the high-level description which has just been given, and the fact that the internal operations of each of the blocks shown in FIG. 2 are well-known to those skilled in the art, one can observe how the four different categories of output information are developed, respectively, on outputs 20, 22, 24, 26. There has thus now been described a preferred embodiment of, and manner of practicing the present invention.

From a relatively high-level point of view, core, cooperative features of the invention methodology can be described as offering a wavelet transform and pattern recognition method for analyzing a subject's heart sounds, including the steps of (a) obtaining heart-sound-relevant acoustic data (heart-sound data) from a selected subject, utilizing a first defined sampling rate, (b) simultaneously gathering ECG data, including pre-selected ECG fiducial data, and (c) processing all of this data, including, with respect to the obtained acoustic data, (1) computing the maximum-overlap discrete wavelet transform (MODWT), (2) locating in time the peaks of the absolute values of the MODWT coefficients respecting each of a pre-selected number (herein six) of wavelet scales, and (3), for each predetermined wavelet scale, interpolating between the located peaks, and subsampling the results of that interpolating behavior, a second defined sampling rate which is no greater than the mentioned first defined sampling rate.

Accordingly, while a preferred embodiment of and manner of practicing the methodology of the present invention have been described and illustrated herein, it is appreciated that variations and modifications may be made without departing from the spirit of the invention.

I claim:

1. A wavelet transform method for analyzing a subject's heart sounds for the purpose of aiding in assessing the condition of the subject's heart, said method comprising
   employing a heart sound detector utilizing a first defined sampling rate, obtaining heart-sound-relevant acoustic data from the subject, and
   processing obtained acoustic data including (a) computing the maximum-overlap discrete wavelet transform (MODWT) for a preselected number of wavelet frequency-band scales having coefficients, (b) determining, and locating the peaks in time of, the absolute values of the MODWT coefficients respecting each frequency-band scale, and (c), for each wavelet frequency-band scale, (1) interpolating between the located peaks, and (2) subsampling the result of said interpolating at another defined sampling rate which is both specific to the relevant frequency-band scale, and no greater than the mentioned first defined sampling rate.

2. A wavelet transform method for analyzing a subject's heart sounds for the purpose of aiding in assessing the condition of the subject's heart, said method comprising
   employing a heart sound detector utilizing a first defined sampling rate, obtaining heart-sound-relevant acoustic data from the subject, and
   processing obtained acoustic data including (a) establishing six, preselected wavelet frequency-band scales having coefficients using the Length-8 wavelet filter from the Daubechies Least Asymmetric Family of wavelet filters (b) computing the maximum-overlap discrete wavelet transform (MODWT) for these six scales, (c) determining, and locating the peaks in time of, the absolute values of the MODWT coefficients respecting each scale, and (d), for each scale, (1) interpolating between the located peaks, and (2) subsampling the result of said interpolating at another defined sampling rate which is both specific to the scale, and no greater than the mentioned first defined sampling rate.

3. The method of claim 2, wherein the six wavelet scales are designated I-VI, inclusive, with scale I having a 3-db filtered range of about 124-250-Hz, scale II a like-filtered range of about 62-124-Hz, scale III a like-filtered range of about 31-62-Hz, scale IV a like-filtered range of about 16-31-Hz, scale V a like-filtered range of about 8-16-Hz, and scale VI a like-filtered range of about 4-8-Hz.

4. The method of claim 3, wherein the first defined sampling rate is no less than about 500-Hz, and there is a specific, and differentiated, second defined sampling rate associated with each of the six wavelet scales, with that which is associated with scale I being no greater than about 500-Hz, that which is associated with scale II being no greater than about 250-Hz, that which is associated with scale III being no greater than about 166.67-Hz, that which is associated with scale IV being no greater than about 83.33-Hz, that which is associated with scale V being no greater than about 41.67-Hz, and that which is associated with scale VI being no greater than about 21.74-Hz.

5. A wavelet transform method for analyzing a subject's heart sounds for the purpose of aiding in assessing the condition of the subject's heart, said method comprising
   employing a heart sound detector utilizing a first defined sampling rate, obtaining heart-sound-relevant acoustic data from the subject,
   processing obtained acoustic data including (a) computing the maximum-overlap discrete wavelet transform (MODWT) for a preselected number of wavelet frequency-band scales having coefficients, (b) determining, and locating the peaks in time of, the absolute values of the MODWT coefficients respecting each scale, and (c), for each preselected wavelet scale, (1) interpolating between the located peaks, and (2) subsampling the result of said interpolating at a another defined sampling rate which is both specific to the scale, and no greater than the mentioned first defined sampling rate, which subsampling produces subsampling values,
   computing the logarithm of the subsampling values produced by said subsampling to generate log values,
   for each wavelet scale, computing the mean average of all related, generated log values, and
   subtracting the computed mean average from each log value to produce a set of associated, resulting values.

6. The method of claim 5, which further comprises, for each one of the preselected wavelet scales, computing a series of feature vectors by aggregating the wavelet-scale-associated resulting values existing within a series of defined-length, next-adjacent temporal window frames which overlap with one another.

7. The method of claim 6, wherein the defined length of each temporal window frame is about 50-milliseconds, and overlapping between next-adjacent window frames is such that the start of an overlapping window frame begins about 12-milliseconds after the start of the just-previous window frame.

8. The method of claim 6, wherein the preselected ECG fiducials include the respective times of QRS and P-wave onsets, and which further includes appending to each feature vector (a) the time difference between the time of the previous QRS onset to the time of the middle of the relevant associated window frame, (b) the time difference between the time of the previous P-wave onset to the time of the beginning of the relevant, associated window frame, and (c) the time difference between the time of the end of the relevant, associated window frame to the time of the next subsequent QRS onset.

9. The method of claim 6, which further includes, for each window frame, computing a multi-dimensional probability for each heart-sound candidate, and utilizing each computed probability as a score.

10. The method of claim 9, which further includes utilizing a Constrained Hidden Markov Model and the activity of a Viterbi search to compute a posterior probability associated with each heart-sound candidate.

11. The method of claim 10, which further includes effectively using information contained in the mentioned subtraction-produced resulting valve closure times which take place in prior-noted heart-sound-S1 and heart-sound S2 segments of the obtained subject data.

12. The method of claim 10, which further includes producing a continuously valued overall confidence score relating to the S3 and S4 heart sounds, with said confidence score-producing being based upon (a) use of the Constrained Hidden Markov Model, and (b) summation of at least the mentioned, computed probability function scores associated with the S3 and S4 heart sounds.

* * * * *

UNITED STATES PATENT AND TRADEMARK OFFICE
CERTIFICATE OF CORRECTION

PATENT NO. : 8,152,731 B2
APPLICATION NO. : 11/704403
DATED : April 10, 2012
INVENTOR(S) : Alex T. Nelson It is certified that error appears in the above-identified patent and that said Letters Patent is hereby corrected as shown below:

Column 8, line 52, please replace "resulting valve" with --resulting values, and in the results of the mentioned Viterbi searching activity, to determine heart-valve--.

Signed and Sealed this
Fourth Day of September, 2012

David J. Kappos
*Director of the United States Patent and Trademark Office*